United States Patent
Suzuki et al.

(10) Patent No.: US 8,236,995 B2
(45) Date of Patent: Aug. 7, 2012

(54) PROCESS FOR PRODUCING PRODUCT OF HYDROGENOLYSIS OF POLYHYDRIC ALCOHOL

(75) Inventors: Nobuyoshi Suzuki, Wakayama (JP); Michio Terasaka, Wakayama (JP)

(73) Assignee: Kao Corporation, Tokyo (JP)

( * ) Notice: Subject to any disclaimer, the term of this patent is extended or adjusted under 35 U.S.C. 154(b) by 366 days.

(21) Appl. No.: 12/515,348

(22) PCT Filed: Nov. 30, 2007

(86) PCT No.: PCT/JP2007/073152
§ 371 (c)(1), (2), (4) Date: May 18, 2009

(87) PCT Pub. No.: WO2008/069120
PCT Pub. Date: Jun. 12, 2008

(65) Prior Publication Data
US 2010/0069685 A1    Mar. 18, 2010

(30) Foreign Application Priority Data
Dec. 5, 2006 (JP) .................................. 2006-328162

(51) Int. Cl.
*C07C 31/18* (2006.01)
(52) U.S. Cl. ....................................... 568/852; 568/885
(58) Field of Classification Search .................. 568/852, 568/885
See application file for complete search history.

(56) References Cited

U.S. PATENT DOCUMENTS

| 6,479,713 B1 | 11/2002 | Werpy et al. |
| 2004/0064003 A1 * | 4/2004 | Werpy et al. ................ 568/885 |
| 2006/0030743 A1 * | 2/2006 | Schubert et al. ............ 568/880 |

FOREIGN PATENT DOCUMENTS

| CN | 1466560 A | 1/2004 |
| WO | WO 02/26678 A2 | 4/2002 |

OTHER PUBLICATIONS

Miyazawa et al., "Glycerol conversion in the aqueous solution under hydrogen over Ru/C+ an ion-exchange resin and its reaction mechanism", Journal of Catalysis., vol. 240, pp. 213-221, 2006.
Shokubai, pp. 438-440, vol. 49, No. 6, Sep. 5, 2007.
Chinese Office Action for Application No. 200780044770.4 dated Nov. 14, 2011.

* cited by examiner

*Primary Examiner* — Sikarl Witherspoon
(74) *Attorney, Agent, or Firm* — Birch, Stewart, Kolasch & Birch, LLP

(57) ABSTRACT

The present invention relates to a process for producing a hydrogenolysis product of a polyhydric alcohol with a high selectivity and high efficiency using a specific catalyst, as well as to a catalyst for hydrogenolysis of a polyhydric alcohol used in the process.

The process for producing a hydrogenolysis product of a polyhydric alcohol includes bringing the polyhydric alcohol into contact with hydrogen in the presence of (A) a catalyst containing at least one metal component selected from among platinum, palladium, and ruthenium, and (B) a catalyst containing a rhenium component. The catalyst for hydrogenolysis of a polyhydric alcohol is used in the process.

5 Claims, No Drawings

PROCESS FOR PRODUCING PRODUCT OF HYDROGENOLYSIS OF POLYHYDRIC ALCOHOL

FIELD OF THE INVENTION

The present invention relates to a process for producing a hydrogenolysis product of a polyhydric alcohol with a high selectivity using a specific catalyst, as well as to a catalyst for hydrogenolysis of a polyhydric alcohol used in the above process.

BACKGROUND OF THE INVENTION

The C3 alcohols are useful as various industrial raw materials, etc. Among these C3 alcohols, diols are widely employed as raw materials for polymers and solvents. In particular, 1,3-propanediol (hereinafter occasionally referred to merely as "1,3-PD"), have been noticed as raw materials of polyesters and polyurethanes. Therefore, it has been recently demanded to develop processes for producing 1,3-PD in an efficient and inexpensive manner.

As the method for producing the 1,3-PD, there are conventionally known (1) a method in which ethylene oxide is hydroformylated to synthesize 3-hydroxypropanal which is then hydrogenated to produce the 1,3-PD, and (2) a method in which acrolein is hydrated to synthesize 3-hydroxypropanal which is then hydrogenated to produce the 1,3-PD.

However, in these conventional methods, the 1,3-PD must be produced by the two-step reactions and via 3-hydroxypropanal as a thermally unstable intermediate product, resulting in high production costs owing to deterioration in yield of the 1,3-PD. For this reason, it has been further demanded to develop a process for producing the 1,3-PD with low costs.

On the other hand, there are also known methods for hydrogenolysis of polyhydric alcohols such as, for example, glycerol, in which the glycerol is converted into 1,2-propanediol (hereinafter occasionally referred to merely as "1,2-PD") and 1,3-PD in a one-step reaction. For example, as the hydrogenolysis methods, there are disclosed a method using a homogeneous catalyst containing tungstic acid and a metal component belonging to Group VIII of the Periodic Table (short-form Periodic Table) (for example, refer to Patent Document 1), a method using a homogeneous catalyst composed of a platinum-group metal complex and an anion source (for example, refer to Patent Document 2), and a method using a rhodium catalyst (for example, refer to Non-Patent Document 1 and 2).

Patent Document 1: U.S. Pat. No. 4,642,394
Patent Document 2: JP 2001-510816A
Non-Patent Document 1: Green Chem., 359, 6, (2004)
Non-Patent Document 2: Catalyst, vol. 49, No. 6, p. 438-441 (2007)

SUMMARY OF THE INVENTION

The present invention relates to:
(1) A process for producing a hydrogenolysis product of a polyhydric alcohol, which includes bringing the polyhydric alcohol into contact with hydrogen in the presence of (A) a catalyst containing at least one metal component selected from among platinum, palladium, and ruthenium, and (B) a catalyst containing a rhenium component;
(2) a catalyst for hydrogenolysis of a polyhydric alcohol, which includes (A) a catalyst containing at least one metal component selected from among platinum, palladium, and ruthenium, and (B) a catalyst containing a rhenium component, in combination; and
(3) a catalyst for hydrogenolysis of a polyhydric alcohol, which includes (A) a catalyst containing at least one metal component selected from among platinum, palladium, and ruthenium, and (B) a catalyst containing a rhenium component, which are supported on a single carrier.

DETAILED DESCRIPTION OF THE INVENTION

Since the conventionally known methods as described in the above Patent Documents and Non-Patent Documents employ a homogeneous platinum-group-metal catalyst and an expensive rhodium catalyst (refer, for example, Non-Patent Document 2), or an organic solvent, these methods are difficult to carry out on an industrial scale at low cost. Thus, there is demand for a method for producing hydrogenolysis of a polyhydric alcohol from the polyhydric alcohol, in particular diols and 1,3-PD from glycerol, with high selectivity and efficiency.

Thus, the present invention relates to a process for producing a hydrogenolysis product of a polyhydric alcohol with high selectivity, as well as to a catalyst for hydrogenolysis of a polyhydric alcohol for use in the process.

The present inventors have found that the aforementioned problem can be solved by use of a catalyst containing at least one metal component selected from among platinum, palladium, and ruthenium, and a rhenium component, as a catalyst for hydrogenolysis of a polyhydric alcohol.

In the process for producing a hydrogenolysis product of a polyhydric alcohol according to the present invention, the polyhydric alcohol is brought into contact with hydrogen in the presence of the hydrogenolysis catalyst to hydrogenolyze the polyhydric alcohol. In the followings, the production process of the present invention is more specifically described.

Polyhydric Alcohol

Examples of the polyhydric alcohol to be hydrogenolyzed in the method of the present invention include aliphatic or alicyclic polyhydric alcohols having 2 to 60 carbon atoms. Specific examples of the polyhydric alcohol include ethylene glycol, diethylene glycol, triethylene glycol, polyethylene glycol, various propanediols, various dipropanediols, various tripropanediols, various butanediols, various dibutanediols, various pentanediols, various pentanetriols, various hexanediols, various hexanetriols, glycerol, diglycerol, triglycerol, polyglycerol, various cyclohexanediols, various cyclohexanetriols, pentaerythritol, trimethylolpropane, and sugar alcohols such as sorbitol and mannitol. Among these polyhydric alcohols, glycerol, diglycerol, triglycerol, polyglycerol, sorbitol, and mannitol are preferred from the industrial viewpoint, with polyhydric alcohols having 2 to 6 hydroxyl groups being more preferred, polyhydric alcohols having 2 and 3 hydroxyl groups being still more preferred, glycerol being particularly preferred.

The hydrogenolysis product of the polyhydric alcohol as used herein means a compound obtained by reacting the polyhydric alcohol with hydrogen to decompose hydroxyl groups thereof. For example, the hydrogenolysis product of glycerol includes C3 diol (number of hydroxyl groups in molecule: 2) and C3 monool (number of hydroxyl groups in molecule: 1).

(A) At Least One Metal Component Selected from Among Platinum, Palladium, and Ruthenium As the aforementioned hydrogenolysis catalyst, a catalyst containing (A) at least one metal component selected from platinum, palladium, and ruthenium (hereinafter may be referred to as "metal component (A)") and a catalyst containing a rhenium component (B) are employed. In the process for producing a hydrogenolysis product of a polyhydric alcohol according to the present invention, the expression "a catalyst containing a metal component (A) and a catalyst containing a rhenium component (B)" also refers to a catalyst containing both a metal component (A) and a rhenium component (B), as is clear in the description hereinbelow.

Specifically, a catalyst containing a metal component (A) and a catalyst containing a rhenium component (B) may be used separately, or a catalyst supporting a metal component (A) and a rhenium component (B) on one single carrier may be used. More specifically, as described in Examples 1 to 4, 6, and 7 of the present invention, the metal component (A) may be employed as a catalyst supported on a carrier, and the rhenium component (B) may be employed as a specific compound and directly added to a reaction solution separately from the metal component (A). As described in Example 5, a catalyst in which both the metal component (A) and the rhenium component (B) are supported on an alumina carrier may be employed.

In the present invention, the metal component (A) is at least one metal component selected from among platinum, palladium, and ruthenium. Among them, platinum and palladium, which belong to the group 10 in the periodic table defined by IUPAC, are more preferred, with platinum being most preferred from the viewpoint of chemical stability. The metal component (A) is preferably employed as a complex catalyst or a solid catalyst, more preferably as a solid catalyst. Particularly, a solid catalyst in which the metal component (A) is supported on a carrier is most preferably used.

No particular limitation is imposed on the carrier supporting at least one metal component (A) selected from platinum, palladium, and ruthenium in the hydrogenolysis catalyst. Examples of the carrier usable in the catalyst include those carriers as described in "Studies in Surface and Catalysis", 1-25, vol. 51, 1989. Specifically, carbons (such as activated carbon), alumina, silica, titania, zirconia, and silica-alumina complex oxide (e.g., zeolite) may be used. Among these carriers, carbon and alumina are preferred. The amount of metal component (A) supported on the carrier is generally from about 0.1 to about 30% by mass, preferably from 1 to 20% by mass, particularly preferably from 2% by mass to 10% by mass, on the basis of a total amount of the carrier and the metal component (A) supported thereon, from the viewpoint of a good catalytic activity.

The amount of (A) at least one metal component selected from among platinum, palladium, and ruthenium may be appropriately determined depending upon kinds of the polyhydric alcohols to be hydrogenolyzed, and is preferably 0.0001 g or more, more preferably from 0.001 to 0.5 g, still more preferably from 0.01 to 0.2 g, in terms of metal elements (platinum, palladium, and ruthenium) on the basis of 1 g of the polyhydric alcohol, from the viewpoint of good conversion rate and selectivity.

(B) Rhenium Component

In the hydrogenolysis catalyst, the rhenium component (B) is used as a catalyst in combination with the metal component(s) (A) selected from platinum, palladium, and ruthenium. Examples of the rhenium component which can be employed in the invention include perrhenate salts such as perrhenic acid, ammonium perrhenate, and potassium perrhenate (particularly alkali metal salts and alkaline earth metal salts); rhenium oxides such as rhenium dioxide, rhenium trioxide, dirhenium trioxide, and dirhenium heptoxide; and methyltrioxorhenium. Of these, perrhenic acid is preferred.

Alternatively, as shown in the Examples, there may be employed a catalyst in which the metal component (A) and the rhenium component are supported on one single carrier, which catalyst may be produced through adding an aqueous solution of a perrhenate salt to a carrier supporting the metal component (A), followed by drying and calcining.

The catalyst supporting the metal component (A) and the catalyst in which the metal component (A) and the rhenium component (B) are supported on one single carrier may be commercial products, or may be prepared through a known method in the art such as the precipitation method, the ion-exchange method, the evaporating-to-dryness method, the spray-drying method, or the kneading method, to thereby causing metal components to be supported on a carrier.

In the hydrogenolysis catalyst, as mentioned above, a variety of compounds (e.g., perrhenic acid and salts thereof, and metal oxides) may be employed as the rhenium component (B) used in combination with the metal component (A). These rhenium compounds may be used singly or in combination of two or more species. From the viewpoints of percent conversion and selectivity, the total amount of rhenium compounds, represented by the ratio by mass of metallic rhenium (Re) to at least one metal component (A) selected from among platinum, palladium, and ruthenium [Re/(A)], is 0.01 to 100, preferably 0.05 to 50, more preferably 0.1 to 30. In one most preferred mode of the catalyst containing the metal component (A) and the rhenium component (B) of the present invention, the metal component (A) is used as a solid catalyst in which the component is supported on a carrier such as carbon or alumina, and perrhenic acid or a salt thereof is used as the rhenium component (B). In another preferred mode, the metal component (A) and the rhenium component (B) are supported on one single carrier.

Reaction Solvent

The process for producing the hydrogenolysis product of a polyhydric alcohol according to the present invention is preferably carried out without using any reaction solvent from the viewpoint of simplified production procedure. However, the hydrogenolysis of the polyhydric alcohol may also be conducted in the presence of the reaction solvent.

The reaction solvent is preferably a protonic solvent. As the reaction solvent, there may be used, for example, at least one solvent selected from the group consisting of water, methanol, ethanol, 1-propanol, 2-propanol, n-butanol, isobutanol, 1,2-propanediol, 1,3-propanediol and ethylene glycol. Among these reaction solvents, preferred are those containing water from the viewpoint of a good reaction efficiency.

The reaction solvent is used in such an amount that the polyhydric alcohol content of the resultant solution is preferably 1% by mass or more, more preferably 5% by mass or more, most preferably 10% by mass or more.

In the process of the present invention, a hydrogen gas as the raw material may be used as such or in the form of a dilute gas prepared by diluting hydrogen with an inert gas such as nitrogen, argon and helium.

No particular limitation is imposed on the reaction conditions, and the conditions may be appropriately determined according to kinds of the polyhydric alcohol and catalyst used in the reaction. In general, the hydrogen pressure is preferably 30 MPa or less and more preferably from 0.1 to 10 MPa as measured at room temperature. The reaction temperature of 80° C. or higher is usually sufficient to carry out the hydrogenolysis. From the viewpoints of a good conversion rate of the polyhydric alcohol by hydrogenolysis as well as a good selectivity to the aimed hydrogenolysis product, the reaction temperature preferably falls within a range of 80 to 240° C., more preferably 100 to 240° C., particularly preferably 120 to 200° C.

The hydrogenolysis reaction may be conducted by either a batch method or a continuous method. The reaction apparatus is not particularly limited, and there may be used apparatuses capable of being pressurized such as an autoclave, fixed-bed flow type apparatuses, etc.

In the process for producing the hydrogenolysis product of a polyhydric alcohol according to the present invention, glycerol is preferably used as the polyhydric alcohol. When using glycerol as the polyhydric alcohol, a mixture composed of 1,3-propanediol, 1,2-propanediol, 1-propanol, 2-propanol, etc., can be produced as hydrogenolysis products.

Also, the present invention provides a catalyst for hydrogenolysis of a polyhydric alcohol which includes (A) a catalyst containing at least one metal component selected from among platinum, palladium, and ruthenium, and (B) a catalyst containing a rhenium component, in combination; and a catalyst for hydrogenolysis of a polyhydric alcohol which includes (A) a catalyst containing at least one metal component selected from among platinum, palladium, and ruthenium, and (B) a catalyst containing a rhenium component, which are supported on a single carrier.

According to the present invention, there can be provided a process for producing hydrogenolysis products of polyhydric alcohols with a high selectivity using a specific catalyst, particularly for producing 1,3-PD from glycerol or diol, as well as catalysts for hydrogenolysis of polyhydric alcohols used in the above process.

EXAMPLES

Example 1

A 500-mL autoclave made of titanium and equipped with a stirrer was charged with 4 g of 5% by mass Pt/C, 7.5 g (0.024 mol) of $HReO_4$ (80% by mass aqueous solution), 12 g of glycerol, and 120 g of water, and an interior of the autoclave was replaced with hydrogen. Thereafter, hydrogen was introduced into the autoclave until reacting 3 MPa, and then the mixture was allowed to react by heating at 160° C. for 3 h. As a result, the percent conversion of glycerol was 49 mol %, and the selectivities to the respective reaction products were 19 mol % for 1,3-PD, 22 mol % for 1,2-PD, 35 mol % for 1-propanol, and 9 mol % for 2-propanol. As used herein, the expression "4 g of 5% by mass Pt/C" refers to a solid catalyst in which platinum is supported on activated carbon, wherein the platinum content of the solid catalyst is 5% by mass. Furthermore, "4 g" means the mass of solid catalyst in the reaction system. The same applies to the following Examples and Comparative Examples. In some cases, the unit "% by mass" may be referred to simply as "%."

After completion of reaction, the reaction solution was found to have a dissolved Pt content of less than 1 ppm and a dissolved Re content of 83 ppm.

The results are shown in Table 1.

Meanwhile, after completion of reaction, the obtained reaction solution was filtered and then analyzed by $^1$H-NMR by means of the following apparatus to conduct a quantitative determination of the reaction products. In addition, the resultant gas component was collected in a gas bag and then analyzed through the following gas chromatographic methods depending upon kinds of gases collected to conduct a quantitative determination of the reaction products.

1) $^1$H-NMR for Solution

Apparatus used: "Mercury 400" available from Varian Inc.; internal standard substance: sodium trimethylsilylpropionate 2) Gas Chromatography for Lower Hydrocarbon Gases Column: "Porapak Q"; 2.1 m×3.2 mmφ; 80-100 mesh; detector: FID; injection temperature: 200° C.; detector temperature: 200° C.; flow rate of He: 60 mL/min 3) Gas Chromatography for CO, $CO_2$ Gases Column: "Molecular Sieve 5A"; detector: FID (with a metanizer fitted between the column and the detector); injection temperature: 80° C.; detector temperature: 80° C.; flow rate of He: 60 mL/min Examples 2 to 4 and Comparative Examples 1 to 3

The same procedure as employed in Example 1 was repeated, except that the reaction was conducted under the conditions shown in Table 1.

The results are shown in Table 1.

Example 5

(Production of Catalyst)

A 0.9% by mass aqueous solution of ammonium perrhenate in an amount of 10 mL was applied onto 6.0 g of a commercially available 5% by mass $Pt/Al_2O_3$ and supported thereon by evaporation to dryness, and then dried at 130° C. for 3 h. Further, the resulting product was calcined at 500° C. for 3 h in an air flow. The thus-obtained catalyst was composed of 5% by mass of Pt and 1% by mass of Re which were supported on alumina ($Al_2O_3$).

(Reaction)

A 500-mL autoclave made of titanium and equipped with a stirrer was charged with 4 g of the above-prepared catalyst, 12 g of glycerol and 120 g of water, and an interior of the autoclave was replaced with hydrogen. Thereafter, hydrogen was introduced into the autoclave until reacting 3 MPa, and then the mixture was allowed to react by heating at 160° C. for 3 h. As a result, the conversion rate of glycerol was 16%, and the selectivities to the respective reaction products were 24 mol % for 1,3-PD, 26 mol % for 1,2-PD, 27 mol % for 1-propanol, and 9 mol % for 2-propanol. After completion of reaction, the reaction solution was found to have a dissolved Pt content of less than 1 ppm and a dissolved Re content of less than 2 ppm.

TABLE 1

|  | Examples | | | |
| --- | --- | --- | --- | --- |
|  | 1 | 2 | 3 | 4 |
| Reaction conditions | | | | |
| Catalyst | 5% Pt/C *1 $HReO_4$ (0.024 mol) | 5% Pt/C $HReO_4$ (0.0024 mol) | 5% Pt/C $MeReO_3$ (0.0024 mol) | 5% $Pt/Al_2O_3$ *2 $HReO_4$ (0.024 mol) |

TABLE 1-continued

|  | | | | |
|---|---|---|---|---|
| Re/(A) metal component (ratio by mass) | 22 | 2.2 | 2.2 | 22 |
| Hydrogen pressure [ambient temperature] (MPa) | 3 | 3 | 3 | 3 |
| Reaction temperature (° C.) | 160 | 160 | 160 | 160 |
| Reaction solvent | Water | Water | Water | Water |
| Reaction results | | | | |
| Percent conversion of glycerol (mol %) | 49 | 9 | 16 | 11 |
| Selectivity (mol %) | | | | |
| 1,3-Propanediol | 19 | 26 | 25 | 30 |
| 1,2-Propanediol | 22 | 40 | 37 | 36 |
| 1-Propanol | 35 | 18 | 18 | 16 |
| 2-Propanol | 9 | 8 | 8 | 13 |
| Ethylene glycol | 0 | 0 | 0 | 0 |
| Other and unknown substances | 15 | 8 | 12 | 5 |

|  | Example | Comparative Examples | | |
|---|---|---|---|---|
|  | 5 | 1 | 2 | 3 |
| Reaction conditions | | | | |
| Catalyst | 5% Pt—1% Re/Al$_2$O$_3$ *3 | 5% Pt/C | HReO$_4$ (0.024 mol) | 5% Pt/C CH$_3$SO$_3$H (6 g) |
| Re/(A) metal component (ratio by mass) | 0.2 | — | — | — |
| Hydrogen pressure [ambient temperature] (MPa) | 3 | 3 | 3 | 3 |
| Reaction temperature (° C.) | 160 | 160 | 160 | 160 |
| Reaction solvent | Water | Water | Water | Water |
| Reaction results | | | | |
| Percent conversion of glycerol (mol %) | 16 | 0 | 4 | 0 |
| Selectivity (mol %) | | | | |
| 1,3-Propanediol | 24 | No reaction products | 0 | No reaction products |
| 1,2-Propanediol | 26 | | 8 | |
| 1-Propanol | 27 | | 20 | |
| 2-Propanol | 9 | | 20 | |
| Ethylene glycol | 0 | | 0 | |
| Other and unknown substances | 14 | | 52 | |

(Note)
*1: 5% Pt/C: 5% by mass Pt/C
*2: 5% Pt/Al$_2$O$_3$: 5% by mass Pt/Al$_2$O$_3$
*3: 5% Pt—1% Re/Al$_2$O$_3$: 5% by mass Pt—1% by mass Re/Al$_2$O$_3$ Examples 6 and 7

In Example 6, a ruthenium catalyst (4 g of 5% by mass Ru/C) was used instead of the platinum catalyst (4 g of 5% by mass Pt/C) employed in Example 1. In Example 7, the procedure of Example 1 was repeated, except that a palladium catalyst (4 g of 5% by mass Pd/C) was used. In Examples 6 and 7, production of diols was remarkably promoted, as compared with the Comparative Examples.

Table 2 shows the results.

TABLE 2

|  | Examples | |
|---|---|---|
|  | 6 | 7 |
| Reaction conditions | | |
| Catalyst | 5% Ru/C *4 HReO$_4$ (0.024 mol) | 5% Pd/C *5 HReO$_4$ (0.024 mol) |
| Re/(A) metal component (ratio by mass) | 22 | 22 |
| Hydrogen pressure [ambient temperature] (MPa) | 3 | 3 |
| Reaction temperature (° C.) | 160 | 160 |
| Reaction solvent | Water | Water |
| Reaction results | | |
| Percent conversion of glycerol (mol %) | 77 | 35 |
| Selectivity (mol %) | | |
| 1,3-Propanediol | 6 | 9 |
| 1,2-Propanediol | 34 | 37 |
| 1-Propanol | 19 | 37 |
| 2-Propanol | 11 | 6 |
| Ethylene glycol | 0 | 0 |

TABLE 2-continued

| | Examples | |
|---|---|---|
| | 6 | 7 |
| Other and unknown substances | 30 | 11 |

(Note)
*4: 5% Ru/C: 5% by mass Ru/C
*5: 5% Pd/C: 5% by mass Pd/C

Industrial Applicability

According to the process of the present invention for producing a hydrogenolysis product of a polyhydric alcohol, a hydrogenolysis product (particularly diols and 1,3-propanediol) can be produced at high selectivity from the polyhydric alcohol (particularly glycerol).

The invention claimed is:

1. A process for producing a 1,3-propanediol from glycerol, which includes bringing the glycerol into contact with hydrogen in the presence of (A) a catalyst containing platinum and (B) a catalyst containing a rhenium component.

2. The process for producing a 1,3-propanediol from glycerol according to claim 1, wherein the rhenium component (B) is at least one species selected from among perrhenic acid or a salt thereof, rhenium oxides, and methyltrioxorhenium.

3. The process for producing a 1,3-propanediol from glycerol according to claim 1, wherein the catalyst containing platinum (A) is a solid catalyst.

4. The process for producing a 1,3-propanediol from glycerol according to claim 1, wherein a protic solvent is employed as a reaction solvent.

5. The process for producing a 1,3-propanediol from glycerol according to claim 4, wherein the protic solvent contains water.

* * * * *